United States Patent
Danziger et al.

(10) Patent No.: US 11,759,648 B2
(45) Date of Patent: *Sep. 19, 2023

(54) TRANSFER OF CARDIAC ARREST DATA BETWEEN DEFIBRILLATORS

(71) Applicant: Physio-Control, Inc., Redmond, WA (US)

(72) Inventors: Benjamin J. Danziger, Kenmore, WA (US); Jil Cruz, Sammamish, WA (US); Dennis M. Skelton, Woodinville, WA (US); Shardul Varma, Kirkland, WA (US); Tyson G. Taylor, Bothell, WA (US)

(73) Assignee: Physio-Control, Inc., Redmond, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/723,058

(22) Filed: Apr. 18, 2022

(65) Prior Publication Data

US 2022/0233874 A1    Jul. 28, 2022

Related U.S. Application Data

(63) Continuation of application No. 17/075,557, filed on Oct. 20, 2020, now Pat. No. 11,331,506.

(60) Provisional application No. 62/962,447, filed on Jan. 17, 2020.

(51) Int. Cl.
*A61N 1/39*    (2006.01)

(52) U.S. Cl.
CPC ......... *A61N 1/3937* (2013.01); *A61N 1/3904* (2017.08); *A61N 1/39044* (2017.08); *A61N 1/3987* (2013.01)

(58) Field of Classification Search
CPC .............................................. A61N 1/39–3993
See application file for complete search history.

(56) References Cited

U.S. PATENT DOCUMENTS

| | | | |
|---|---|---|---|
| 5,697,955 A | 12/1997 | Stolte | |
| 6,040,773 A | 3/2000 | Vega et al. | |
| 6,360,120 B1 * | 3/2002 | Powers | A61N 1/3925 600/510 |
| 6,560,485 B2 | 5/2003 | Herleikson | |
| 9,844,658 B2 * | 12/2017 | Jensen | A61N 1/0492 |
| 9,916,436 B2 | 3/2018 | Bielstein | |
| 11,331,506 B2 * | 5/2022 | Danziger | A61N 1/3937 |
| 2001/0034488 A1 | 10/2001 | Policker et al. | |

(Continued)

OTHER PUBLICATIONS

Non-Final Office Action for U.S. Appl. No. 17/075,557, dated Oct. 21, 2021.

*Primary Examiner* — Eric D. Bertram
(74) *Attorney, Agent, or Firm* — McDonnell Boehnen Hulbert & Berghoff LLP

(57) ABSTRACT

An example method is performed by a current defibrillator and includes determining that a memory embedded within a therapy cable coupled to the current defibrillator stores data indicative of a previous shock delivered to a patient, the previous being delivered using a previous defibrillator. The method also includes obtaining the data indicative of the previous shock, and setting an energy level for a subsequent shock based on the data indicative of the previous shock. The method further includes delivering the subsequent shock to the patient at the energy level for the subsequent shock.

20 Claims, 9 Drawing Sheets

(56) References Cited

U.S. PATENT DOCUMENTS

| | | |
|---|---|---|
| 2003/0187339 A1 | 10/2003 | Carim |
| 2004/0162586 A1* | 8/2004 | Covey .................. A61N 1/0472 |
| | | 607/5 |
| 2015/0094782 A1* | 4/2015 | Prew ...................... A61N 1/046 |
| | | 607/142 |
| 2020/0360706 A1* | 11/2020 | Bielstein ............ A61N 1/36146 |
| 2021/0146146 A1* | 5/2021 | Hoelscher ............ A61N 1/3993 |
| 2021/0220660 A1* | 7/2021 | Danziger ............. A61N 1/3904 |
| 2021/0236804 A1* | 8/2021 | Jensen .................. A61N 1/046 |

* cited by examiner

TRANSFER OF CARDIAC ARREST DATA BETWEEN DEFIBRILLATORS

CROSS-REFERENCE TO RELATED APPLICATION

The present application is a continuation of, and claims priority to, U.S. patent application Ser. No. 17/075,557 filed on Oct. 20, 2020, and issued as U.S. Pat. No. 11,331,506, which claims priority to U.S. Provisional Pat. App. No. 62/962,447 filed on Jan. 17, 2020, each of which is hereby incorporated by reference in its entirety.

BACKGROUND

During a cardiac arrest, an automated external defibrillator (AED) can be utilized before an emergency medical services (EMS) crew arrives. For example, when a patient undergoes cardiac arrest, it is common for nearby individuals to begin cardiopulmonary resuscitation (CPR). If an AED is close at hand, those individuals responding to this cardiac arrest situation will (hopefully) use that AED before the EMS crew arrives.

The AED can provide potentially lifesaving defibrillation treatment. For instance, the AED is configured to supply a charge through the patient's heart via a set of defibrillation pads of a therapy cable. The defibrillation pads are located at a first end of the therapy cable and applied to chest of a patient. At a second of the therapy cable, a connector couples the therapy cable to an electrical source of the AED that is configured to generate a shock.

When the EMS crew arrives, the EMS crew assumes the care of the patient undergoing the cardiac arrest. For example, such care typically includes the EMS crew switching the patient from the AED to a more advanced defibrillator, such as a monitor defibrillator. After the EMS crew has switched the patient to the more advanced defibrillator, the EMS crew may continue CPR and will also secure the patient for potential transport. This could include removing the existing defibrillation pads from the chest of the patient and then placing new defibrillation pads on the patient. Alternatively, and if possible, the EMS crew will unplug the therapy cable from the AED and then plug the same therapy cable into the more advanced defibrillator, either directly or through an adapter. With this approach, the existing defibrillation pads can be used for subsequent monitoring and/or defibrillation.

SUMMARY

Within examples described herein, systems and methods are described that include using a memory embedded within a therapy cable to store data indicative of a previous shock delivered to a patient.

Within additional examples described herein, systems and methods are described that include transferring patient data obtained by a previous defibrillator to a current defibrillator that is used to provide care for the patient.

The features, functions, and advantages that have been discussed can be achieved independently in various examples or may be combined in yet other examples. Further details of the examples can be seen with reference to the following description and drawings.

BRIEF DESCRIPTION OF THE FIGURES

The novel features believed characteristic of the illustrative examples are set forth in the appended claims. The illustrative examples, however, as well as a preferred mode of use, further objectives and descriptions thereof, will best be understood by reference to the following detailed description of an illustrative example of the present disclosure when read in conjunction with the accompanying drawings, wherein:

DETAILED DESCRIPTION

Disclosed examples will now be described more fully hereinafter with reference to the accompanying drawings, in which some, but not all of the disclosed examples are shown. Indeed, several different examples may be described and should not be construed as limited to the examples set forth herein. Rather, these examples are described so that this disclosure will be thorough and complete and will fully convey the scope of the disclosure to those skilled in the art.

Currently, when a healthcare provider, such as a member of an EMS crew, assumes the care of a patient undergoing cardiac arrest, the defibrillator utilized by the EMS crew is not able to determine if any shocks were previously applied to patient. Consequently, the defibrillator is also unable to determine the energy level of any previous shocks delivered to the patient by another defibrillator, such as an AED, if indeed the other defibrillator was used to administer a shock.

Example methods and systems describe providing a current defibrillator with data indicative of a previous shock delivered to a patient by a previous defibrillator. In some examples, data obtained from the previous defibrillator can be stored in a memory embedded within a therapy cable of the previous defibrillator. This data can, for example, include an energy level of a most recent shock, how many shocks were given, what type of fibrillation was observed, measured waveforms (e.g., ECG data before and after delivery of a shock), and/or other information. With this approach, when the therapy cable is unplugged from the previous defibrillator and plugged into the current defibrillator, a processor of the current defibrillator can read the data from the memory of the therapy cable. The current defibrillator and/or an operator of the current defibrillator can then use the data to help improve treatment of a patient. If the patient is delivered to a hospital, use of the data can help improve patient treatment at the hospital as well.

In other examples, when a medical provider assumes treatment of a patient using a current defibrillator, the current defibrillator can wirelessly receive data regarding the patient that was previously obtained and recorded by a previous defibrillator. For instance, the current defibrillator can wirelessly receive the data directly from the previous defibrillator. Alternatively, the previous defibrillator can transmit the data to a server in a network, and the current defibrillator can wirelessly receive the data from the server.

Further details and features of these methods and systems are described hereinafter with reference to the figures.

Figure 1:
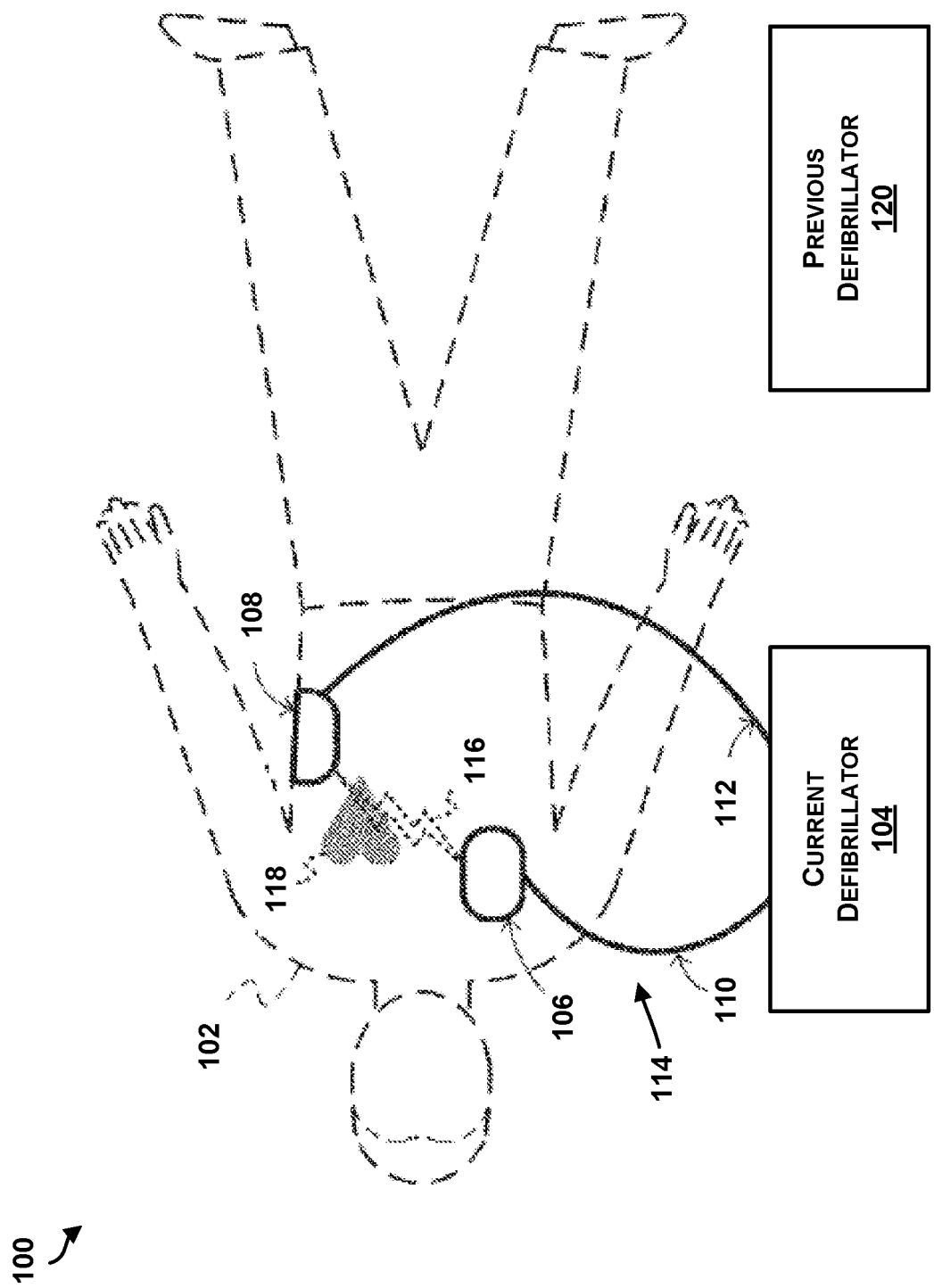
FIG. 1 illustrates an example defibrillation scene, according to an example implementation.
Figure 2:
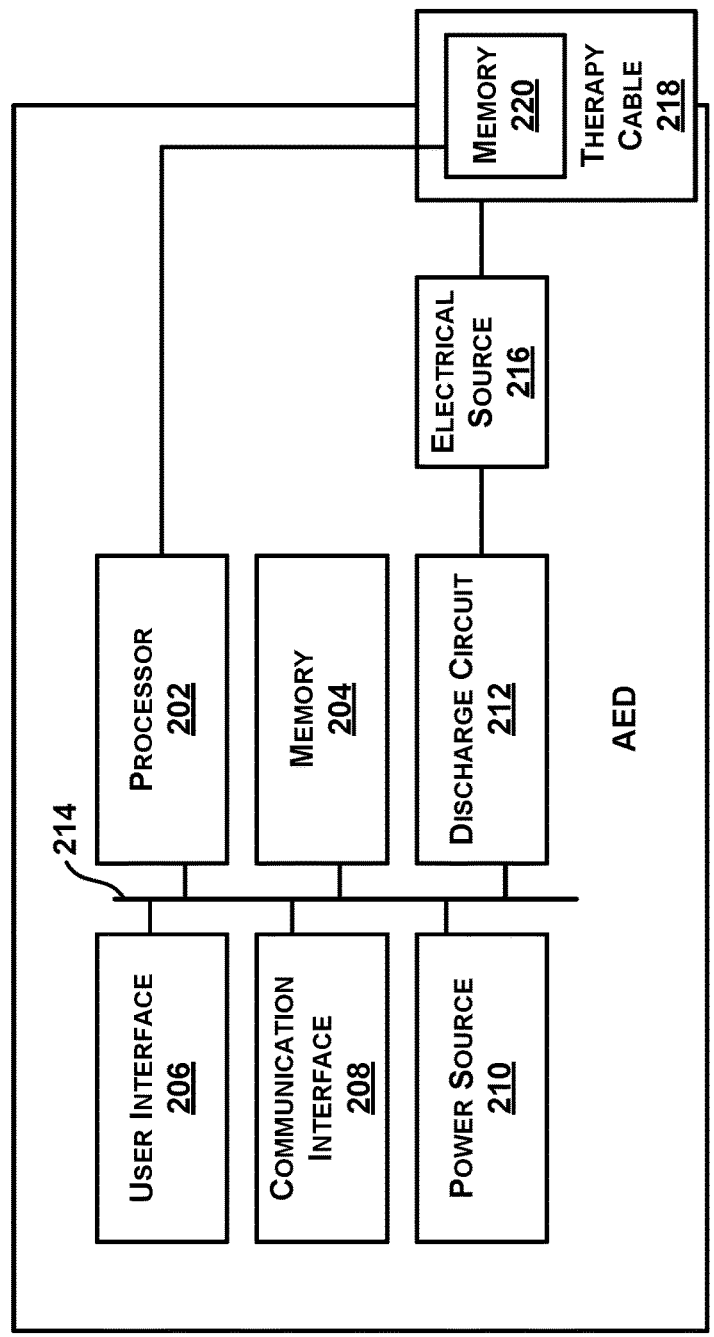
FIG. 2 illustrates a block diagram of an example defibrillator, according to an example implementation.

Referring now to the figures, FIG. 1 illustrates an example defibrillation scene 100. As shown in FIG. 1, a patient 102 is lying on their back. Patient 102 could be a patient in a public space, a home, a pre-hospital environment, or even a hospital. A current defibrillator 104 is currently being used to treat patient 102. As shown in FIG. 2, defibrillation pads 106, 108 of current defibrillator 104 are applied to a chest of patient 102. Defibrillation pad 106 is coupled to current defibrillator 104 via an electrode lead 110. Defibrillation pad 108 is coupled to current defibrillator 104 via an electrode lead 112. Defibrillation pads 106, 108 and electrode leads 110, 112 are collectively referred to as a therapy cable 114. Current defibrillator 104 can be used to deliver, via therapy cable 114, a shock 116. Shock 116 can go through a heart 118 of patient 102, in an attempt to restart heart 118, for saving the life of patient 102.

Defibrillation scene 100 also includes a previous defibrillator 120. Previous defibrillator 120 may have been used to deliver a shock to patient 102 before current defibrillator 104 is used to treat patient 102. In some examples, therapy cable 114 may be the therapy cable that is stored with and intended to be used with previous defibrillator 120. Therapy cable 114 may have been unplugged from previous defibrillator 120 via a connector (not shown) and plugged into current defibrillator 104. Alternatively, therapy cable 114 can be stored and intended to be used with current defibrillator 104, and previous defibrillator 120 can include a separate therapy cable (not shown).

Current defibrillator 104, and likewise previous defibrillator 120, can be one of multiple different types, each with different sets of features and capabilities. As one example, one or both of current defibrillator 104 and previous defibrillator 120, can be an AED, such as a public access defibrillator AED. An AED can make a decision as to whether or not to deliver a shock to a patient automatically. For example, an AED can sense physiological conditions, such as shockable heart rhythms, of a patient via defibrillation pads applied to the patient, and make the decision based on an analysis of the patient's heart. Further, an AED can either deliver the shock automatically, or instruct a user to deliver a shock, e.g., by pushing a button. AEDs can be operated by medical professionals as well as people who are not in the medical profession, such as policemen, firemen, or even a person with first-aid and CPR/AED training. AEDs can be located in public spaces or homes so that lifesaving treatment can hopefully be initiated before medical professionals arrive.

As another example, one or both of current defibrillator 104 and previous defibrillator 120 can be a more advanced device, such as a monitor defibrillator. Monitor defibrillators are intended to be used by trained medical professionals, such as doctors, nurses, paramedics, emergency medical technicians, etc. As the name suggests, a monitor defibrillator is a combination of a monitor and a defibrillator. As a defibrillator, a monitor defibrillator can be one of different varieties, or even versatile enough to be able to switch among different modes that individually correspond to the varieties. One variety is that of an automated defibrillator, which can determine whether a shock is needed and, if so, charge to a predetermined energy level and instruct the user to deliver the shock. Another variety is that of a manual defibrillator, where the user determines the need and controls delivery of the shock. As a patient monitor, the monitor defibrillator has features additional to what is needed for operation as a defibrillator. These features can be for monitoring physiological indicators of a patient in an emergency scenario, for instance.

FIG. 2 illustrates an example AED 200. In FIG. 2, AED 200 includes a processor 202, a memory 204, a user interface 206, a communication interface 208, a power source 210, and a discharge circuit 212, each connected to a communication bus 214. AED 200 also includes an electrical source 216 connected to discharge circuit 212, and a therapy cable 218 connected to electrical source 216.

Memory 204 may include one or more computer-readable storage media that can be read or accessed by processor 202. The computer-readable storage media can include volatile and/or non-volatile storage components, such as optical, magnetic, organic or other memory or disc storage, which can be integrated in whole or in part with processor 202. The non-transitory data storage is considered non-transitory computer readable media. In some examples, the non-transitory data storage can be implemented using a single physical device (e.g., one optical, magnetic, organic or other memory or disc storage unit), while in other examples, the non-transitory data storage can be implemented using two or more physical devices.

The non-transitory data storage thus is a computer readable medium, and instructions are stored thereon. The instructions include computer executable code.

Processor 202 may be a general-purpose processor or a special purpose processor (e.g., digital signal processor, application specific integrated circuit, etc.). Processor 202 may receive inputs from other components of AED 200 and process the inputs to generate outputs that are stored in the non-transitory data storage. Processor 202 can be configured to execute instructions (e.g., computer-readable program instructions) that are stored in the non-transitory data storage and are executable to provide the functionality of the AED described herein. For example, processor 202 can execute instructions for determining data indicative of a shock delivered to a patient, and storing the data in memory 204 and/or a memory 220 of therapy cable 218. Processor 202 can also execute instructions for analyzing physiological data, and storing a result of the analysis in memory 204 and/or memory 220.

User interface 206 can take any of a number of forms. For example, user interface 206 may include output devices, which can be visual, audible or tactile, for communicating to a user. An output device can be configured to output a warning, which warns or instructs the patient or a bystander to do something. An output device can be a light or a screen to display what is detected and measured, and provide visual feedback to the rescuer for their resuscitation attempts. User interface 206 may also include a speaker, to issue voice prompts or sounds. User interface 206 may additionally include input devices for receiving inputs from users. Such input devices may include various controls, such as push-buttons, keyboards, touchscreens, or a microphone.

Communication interface 208 may be one or more wireless interfaces and/or one or more wireline interfaces that allow for both short-range communication and long-range communication to one or more networks or to one or more remote devices. Such wireless interfaces may provide for communication under one or more wireless communication protocols, such as Bluetooth, Wi-Fi (e.g., an institute of electrical and electronic engineers (IEEE) 802.11 protocol), Long-Term Evolution (LTE), cellular communications, near-field communication (NFC), and/or other wireless communication protocols. Such wireline interfaces may include an Ethernet interface, a Universal Serial Bus (USB) interface, or similar interface to communicate via a wire, a twisted pair of wires, a coaxial cable, an optical link, a fiber-optic link, or other physical connection to a wireline network. Communication interface 208 thus may include hardware to enable communication between AED 200 and other devices (not shown). The hardware may include transmitters, receivers, and antennas, for example.

Power source 210 may include battery power, or a wired power means such as an AC power connection.

Electrical source 216 can be configured to store electrical energy in the form of an electrical charge, when preparing for delivery of a shock. Discharge circuit 212 can be controlled to permit the energy stored in electrical source 216 to be discharged to defibrillation pads of therapy cable 218. Discharge circuit 212 can include one or more switches, such as an H-bridge. Processor 202 can instruct discharge circuit 212 to output a shock using one of various energy levels. The energy levels can range from 50 Joules to 360 Joules. For instance, for an adult, processor 202 can select an energy level from an adult energy sequence that includes energy levels of 200 Joules, 300 Joules, and 360 Joules. Whereas, for a pediatric patient, processor 202 can select an energy level from a pediatric energy sequence that includes energy levels of 50 Joules, 75 Joules, and 90 Joules.

Therapy cable 218 can be detachable from a housing of AED 200 by way of a connector. The connector can be a tabbed, male connector that is compatible with a port of AED 200.

Memory 220 of therapy cable can be a non-volatile memory that is controllable and electrically erasable by processor 202. For instance, memory 220 can be a one-wire electrically erasable programmable read-only memory (EEPROM). Processor 202 can access memory 220 using pins of the connector of therapy cable 218. Prior to use of AED 200, memory 220 can store a model number or serial number of therapy cable 218, an expiration date of therapy cable 218, and/or a date of manufacture of therapy cable 218. When AED 200 is in use, processor 202 can write additional data to memory 220 as described more fully below. Optionally, processor 202 can also read data from memory 220, and write that data to memory 204.

In some examples, therapy cable 218 can include a wireless communication interface (not shown). The wireless communication interface can allow therapy cable 218 to broadcast data after therapy cable 218 is unplugged from AED 200. For instance, the wireless communication interface can include a low power system on a chip (SoC) or wireless integrated circuit (IC). The power supply for the wireless communication interface could be a capacitor embedded in therapy cable 218, and the capacitor can be charged by AED 200 when therapy cable 218 is plugged in to AED 200.

The defibrillation pads of therapy cable 218 can be similar to defibrillation pads 106, 108 of FIG. 1. The defibrillation pads can include sensors that output physiologic monitoring data measurements to processor 202. For example, the defibrillation pads can include sensors that measure heart electrical activity such as electrocardiogram (ECG).

After a shock is delivered, or in parallel with the instructing of discharge circuit 212 to deliver a shock, processor 202 can store data indicative of the shock in memory 204 and/or memory 220. The data indicative of the shock can include one or any combination of an energy level of the shock, a timestamp associated with the shock, an identification of AED 200, such as a model number or serial number of AED 200, an indication of a number of the shock (e.g., an indication that the shock is the first shock, second, shock, third shock, etc.), and an error code associated with the shock.

Additionally or alternatively, during a patient care event, processor 202 can determine and store other data in memory 204 and/or memory 220. As one example, processor 202 can determine and store data indicating that return of spontaneous circulation (ROSC) was achieved after delivering a shock. Processor 202 could determine that ROSC was achieved using one or more of the following techniques: inferring that ROSC was achieved via electrical signals; detect a motion artifact that does not correspond to compressions or moving a patient; determining whether a trend after serval complete PQRST waveforms shows degradation; identifying respiratory breath from ECG; receiving information (e.g., wirelessly) from an accessory configured to deliver information to AED 200, such as blood pressure, SpO2, CO2, etc.; voice recognition that identifies keywords such as "I feel a pulse!" Processor 202 can also determine that ROSC was achieved after delivering a shock based on receiving an indication from another device. For instance, processor 202 can send data obtained by AED 200 to a server in network. The server, in turn, can analyze the data to determine whether or not the data is indicative of ROSC being achieved (e.g., using any of the techniques noted above), and send to AED 200 data indicative of whether or not ROSC was achieved.

As another example, processor 202 can analyze ECG data, determine a fibrillation type using the ECG data, and store an indication of the fibrillation type. Ventricular fibrillation (VF) can be qualified as either refractory VF or recurrent VF. Refractory VF refers to VF that persists despite shock delivery. This is in contrast to recurrent VF, which is VF that re-appears after it had previously been terminated. The indication of fibrillation type could therefore include an indication of refractory VF or an indication of recurrent VF. Similarly, processor 202 can analyze ECG data, determine a coarseness of a VF waveform, and store an indication of the coarseness of the VF waveform. As still another example, processor 202 can store an initial rhythm measured by AED 200, such as a few seconds of raw ECG data that is obtained before delivery of any shocks. Processor 202 can also determine and store data indicative of an algorithm used to measure the initial rhythm, such as data indicative of a name of the algorithm.

As another example, processor 202 can determine and store data indicating whether a rhythm detected after delivery of a shock is shockable or non-shockable. For instance, if processor 202 detects a non-shockable rhythm (e.g., pulseless electrical activity or asystole) after delivery of a shock, processor 202 can store in memory 204 and/or memory 220 data indicating that a non-shockable rhythm was detected after delivery of the shock. Whereas, if processor 202 detects a shockable rhythm (e.g., VF or ventricular tachycardia) after delivery of a shock, processor 202 can store in memory 204 and/or memory 220 data indicating that a shockable rhythm was detected after delivery of the shock.

As yet another example, processor 202 can determine whether CPR is being performed, and then store in memory 204 and/or memory 220 data indicative of whether or not CPR was performed on the patient. For example, processor 202 can determine whether CPR is being performed based on analysis of impedance signals received from the defibrillation pads of therapy cable 218. As another example, processor 202 can determine whether CPR is being performed based on an analysis of an ECG signal. CPR results in a very rhythmic change in ECG signal. Processor 202 can detect such a change using signal processing. Such processing can involve providing the ECG signal to a trained neural network that is configured to output an indication of whether the ECG signal is indicative of CPR being performed. The neural network can be trained using ECG signals that are known to have been captured while CPR is being performed. The data indicative of whether or not CPR was performed can include data for individual compressions (e.g., compression rate data). Additionally or alternatively, the data indicative of whether or not CPR was performed can include a binary indication (e.g., yes or no), or a qualitative indication (e.g., no CPR; bad CPR; moderate CPR; good CPR; great CPR). Processor 202 can also determine and store in memory 204 and/or memory 220 data indicative of whether or not AED 200 advised a user to continue CPR after a shock was delivered.

As yet another example, processor 202 can determine and then store in memory 204 and/or memory 220 data indicative of whether any noise was detected during the patient care event. Examples of noise include motion of the patient (e.g., chest compressions performed during analysis of the patient's heart), the presence of an additional defibrillator attached to the patient, detection of a pacemaker or other implantable device. In one example, processor 202 can detect such noise through signal processing of an ECG signal. Such signal processing can include performing a Fourier transform, and analyzing the resulting frequency information. For instance, implanted electrical signal stimulator usually pulse very rhythmically and, as a result, may be detectable from a Fourier transform of an ECG signal.

Figure 3:
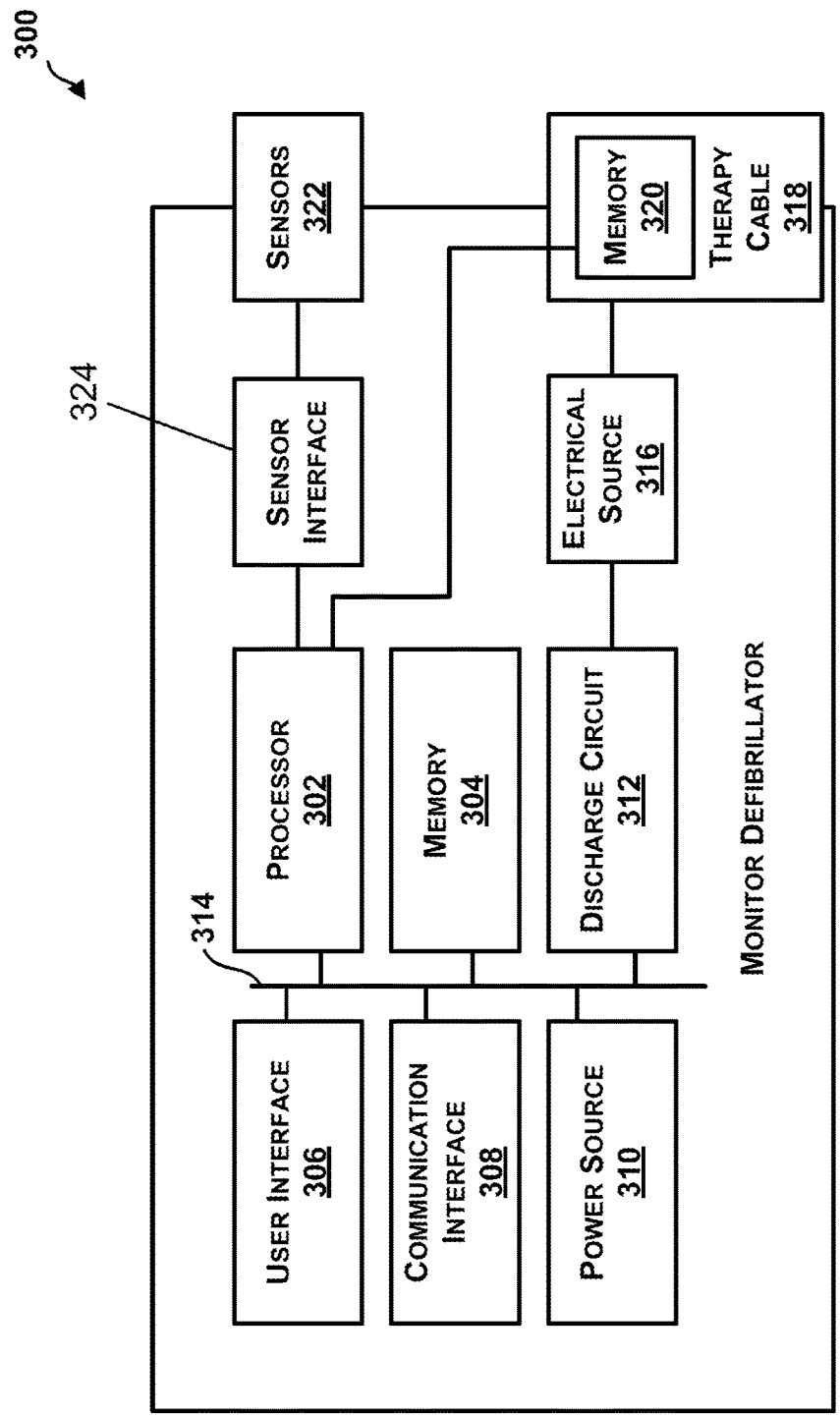
FIG. 3 illustrates a block diagram of another example defibrillator, according to an example implementation.

FIG. 3 illustrates an example monitor defibrillator 300. Like AED 200 of FIG. 2, monitor defibrillator 300 includes a processor 302, a memory 304, a user interface 306, a communication interface 308, a power source 310, and a discharge circuit 312, each connected to a communication bus 314. Monitor defibrillator 300 also includes an electrical source 316 connected to discharge circuit 312, and a therapy cable 318 connected to electrical source 316. Further, therapy cable 318 includes a memory 320.

Unlike AED 200, monitor defibrillator 300 includes physiologic monitoring sensors 322 and a sensor interface 324 that couples physiologic monitoring sensors 322 with processor 302. Physiologic monitoring sensors 322 allow for monitoring physiological indicators of a patient. Any number or type of sensors may be used depending on treatment or monitoring of the patient. In many instances, a variety of sensors are used to determine a variety of physiologic monitoring data. Physiologic monitoring data can include vital sign data (e.g., heart rate, respiration rate, blood pressure, and body temperature), as well as signals from other sensors described herein. In addition, physiologic monitoring data can also include treatment monitoring data, such as location at which an endotracheal tube has been placed or other sensor context information. The physiologic monitoring data can include timestamps associated with a time of collection and may be considered a measurement at a specific time. In some instances herein, physiologic monitoring data refers to one measurement and data associated with the one measurement, and in other instances, physiologic monitoring data refers to a collection of measurements as context indicates.

Physiologic monitoring sensors 322 can include sensors that measure heart electrical activity such as electrocardiogram (ECG), saturation of the hemoglobin in arterial blood with oxygen (SpO2), carbon monoxide (carboxyhemoglobin, COHb) and/or methemoglobin (SpMet), partial pressure of carbon dioxide (CO2) in gases in the airway by means of capnography, total air pressure in the airway, flow rate or volume of air moving in and out of the airway, blood flow, blood pressure such as non-invasive blood pressure (NIBP) or invasive blood pressure (IP) by means of a catheter, core body temperature with a temperature probe in the esophagus, oxygenation of hemoglobin within a volume of tissue (rSO2), indicating level of tissue perfusion with blood and supply of oxygen provided by that perfusion, and so forth.

Outputs, e.g., signals, from physiologic monitoring sensors 322 are conveyed to processor 302 by way of sensor interface 324. Processor 302 records the signals and uses the signals for vital sign qualification and caregiver feedback. In some examples, outputs from physiologic monitoring sensors 322 or data derived from an analysis of the outputs can be recorded in a patient care record of monitor defibrillator 300 and delivered to subsequent entities (e.g., hospital emergency department, etc.) via communication interface 308.

Within one example, in operation, when instructions stored in memory 304 are executed by processor 302, monitor defibrillator 300 is caused to perform a set of acts including determining that memory 320 embedded within therapy cable 318 stored data indicative of a previous shock delivered to a patient using another defibrillator. The set of acts then include obtaining the data indicative of the previous shock, and setting an energy level for a subsequent shock based on the data indicative of the previous shock. Further, the set of acts includes delivering the subsequent shock to the patient at the energy level.

Within another example, in operation, when instructions stored in memory 304 are executed by processor 302, monitor defibrillator 300 is caused to perform a set of acts including wirelessly receiving data indicative of a previous shock delivered to a patient by another defibrillator. The set of acts then includes setting an energy level for a subsequent shock based on the data indicative of the previous shock, and delivering the subsequent shock to the patient at the energy level.

In line with the discussion above, during a patient care event, a user can assume care of a patient, and provide care using a current defibrillator. Further, the current defibrillator can obtain data that was determined and stored by a previous defibrillator that was previously used to provide care to the patient during the patient care event. FIGS. 4-9 are block diagrams illustrating acts that can be carried out in conjunction with use of the current defibrillator and the previous defibrillator in such a scenario.

Figure 4:
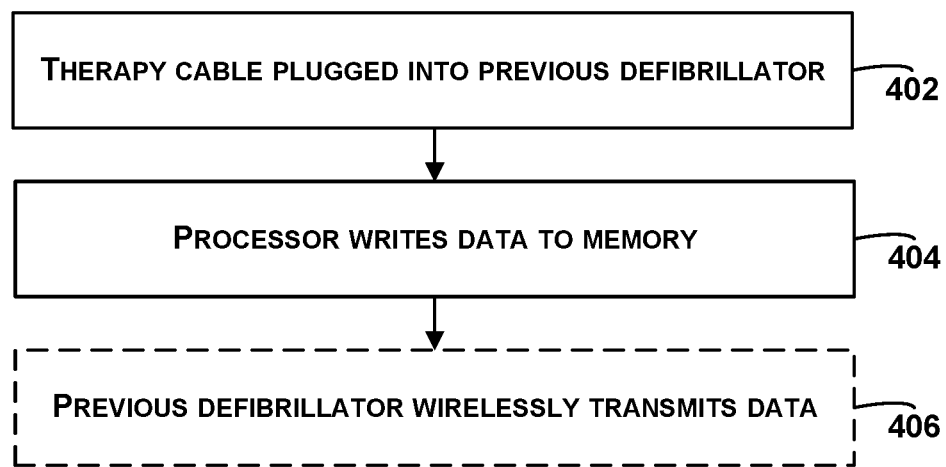
FIG. 4 is a block diagram illustrating example acts that can be carried out in conjunction with use of a defibrillator, according to an example implementation.

More specifically, FIG. 4 is a block diagram illustrating a set of acts that can be carried out in conjunction with use of a previous defibrillator during a patient care event. In some examples, the previous defibrillator can be an AED, such as AED 200 of FIG. 2. In other examples, the previous defibrillator can be a monitor defibrillator, such as monitor defibrillator 300 of FIG. 3.

As shown in FIG. 4, at block 402, a therapy cable is plugged into the previous defibrillator. The therapy cable can be plugged into a port of the previous defibrillator using a connector of the therapy cable, or the therapy cable can be plugged into an adapter cable that, in turn, is plugged into a port of the previous defibrillator. Prior to or after plugging the therapy cable into the previous defibrillator, defibrillation pads of the therapy cable are applied to a chest of the patient. The previous defibrillator is then used to treat and/or monitor the patient.

At step 404, during the patient care event, a processor of the previous defibrillator writes data to a memory. The memory can be a memory of the previous defibrillator and/or a memory embedded within the therapy cable. The data that is written to one or both of the memories can include any of the data discussed above in conjunction with FIG. 2. For instance, the data can include one or any combination of: data indicative of a shock, such as an energy level, timestamp, identification of the previous defibrillator, number of the shock; data indicating that ROSC was achieved after delivering a shock; data indicative of a fibrillation type; data indicative of a coarseness of a VF waveform measured by the previous defibrillator; data indicative of an initial rhythm measured by the previous defibrillator; data indicative of whether a post-shock rhythm is shockable or non-shockable; data indicative of an algorithm used to measure the initial rhythm; data indicative of an error code associated with a shock; data indicative of whether or not CPR was performed on the patient; data indicative of whether or not the previous defibrillator advised a user to continue CPR after a shock was delivered; data indicative of noise detected by the previous defibrillator; and a timestamp indicating when the therapy cable was plugged in.

Optionally, at step 406, the previous defibrillator wirelessly transmits data. As one example, the previous defibrillator can wirelessly transmit data directly to another defibrillator. With this approach, the previous defibrillator may search for nearby defibrillators and connect with another defibrillator before wirelessly transmitting the data. As another example, the previous defibrillator can wirelessly transmit data to a server in a network. The previous defibrillator can wirelessly transmit data to the server at one or more of various times throughout the patient care event. For instance, the previous defibrillator can wirelessly transmit data after each shock is delivered, when the therapy cable is unplugged, and/or when the previous defibrillator is powered off. In some examples, the previous defibrillator can wirelessly transmit data directly to another defibrillator and also wirelessly transmit data to a server in a network.

The wireless transmission at step 406 can include wirelessly transmitting data stored in a memory of the previous defibrillator and/or data stored in a memory of the therapy cable. Further, the previous defibrillator can wirelessly transmit the data using either a wireless communication interface of the previous defibrillator, such as a wireless communication interface located within a housing of the previous defibrillator or a wireless communication interface plugged into a port of the previous defibrillator. Additionally or alternatively, the previous defibrillator can wirelessly transmit the data using a wireless communication interface embedded within the therapy cable. Such wireless transmission via a wireless communication interface embedded within the therapy cable can, in some examples, occur after the therapy cable is unplugged from the previous defibrillator. For instance, unplugging the therapy cable can trigger the wireless communication interface within the therapy cable to wirelessly transmit data or search for a nearby defibrillator to wirelessly transmit data to. In a similar manner, unplugging the therapy cable can trigger the wireless communication interface of the previous defibrillator to wirelessly transmit data or search for a nearby defibrillator to wirelessly transmit data to.

Figure 5:
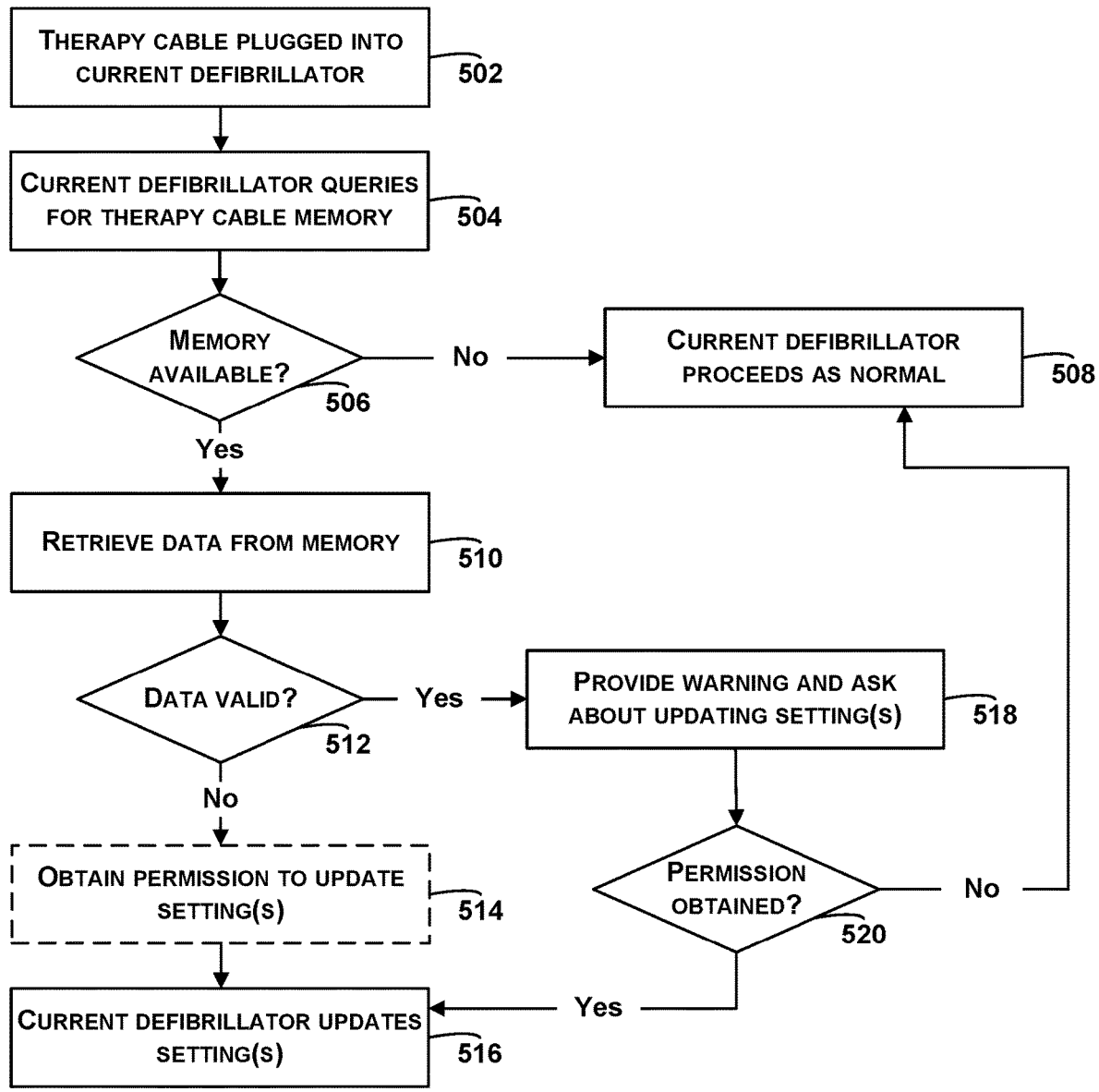
FIG. 5 is another block diagram illustrating example acts that can be carried out in conjunction with use of a defibrillator, according to an example implementation.
Figure 6:
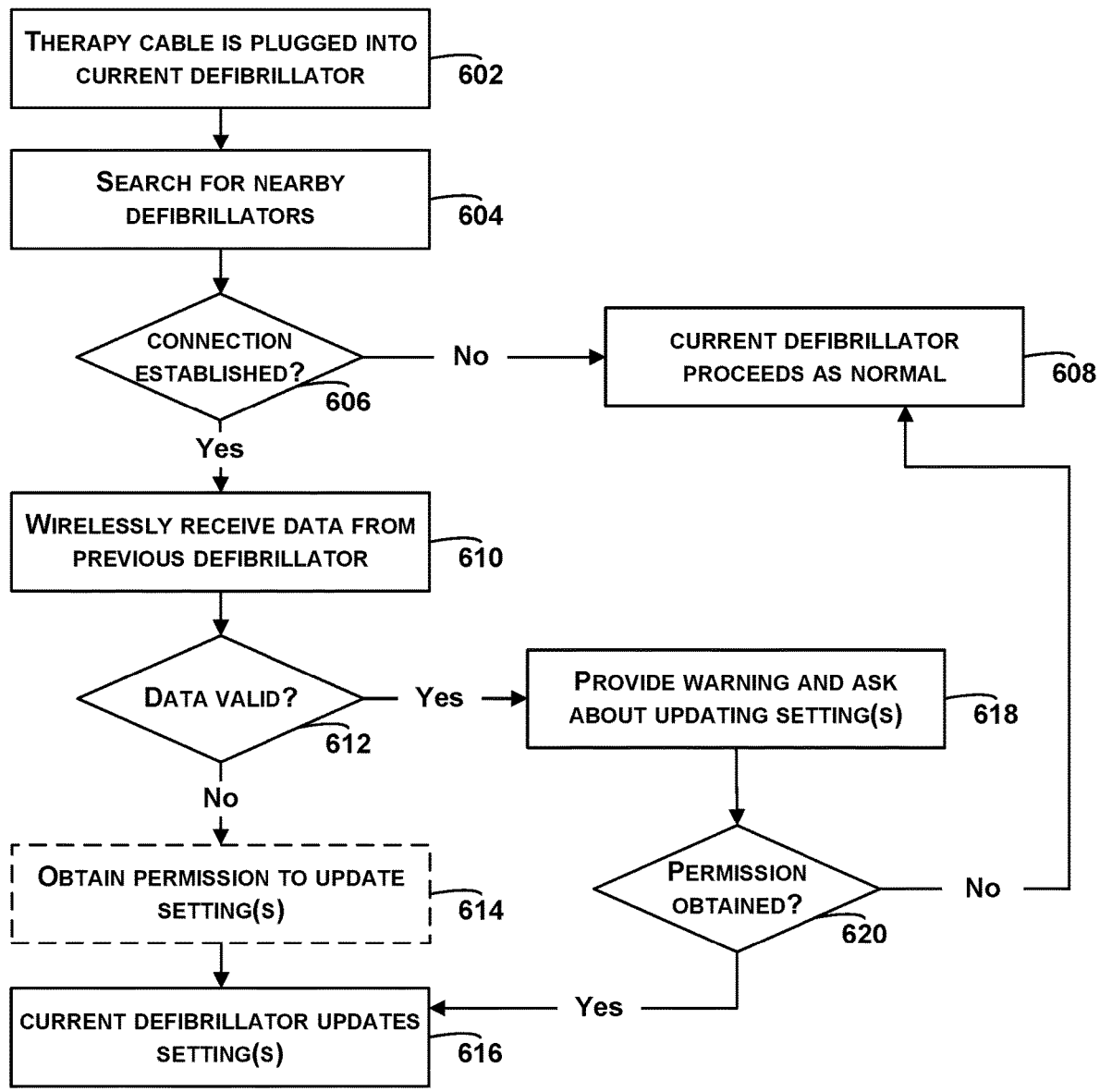
FIG. 6 is still another block diagram illustrating example acts that can be carried out in conjunction with use of a defibrillator, according to an example implementation.
Figure 7:
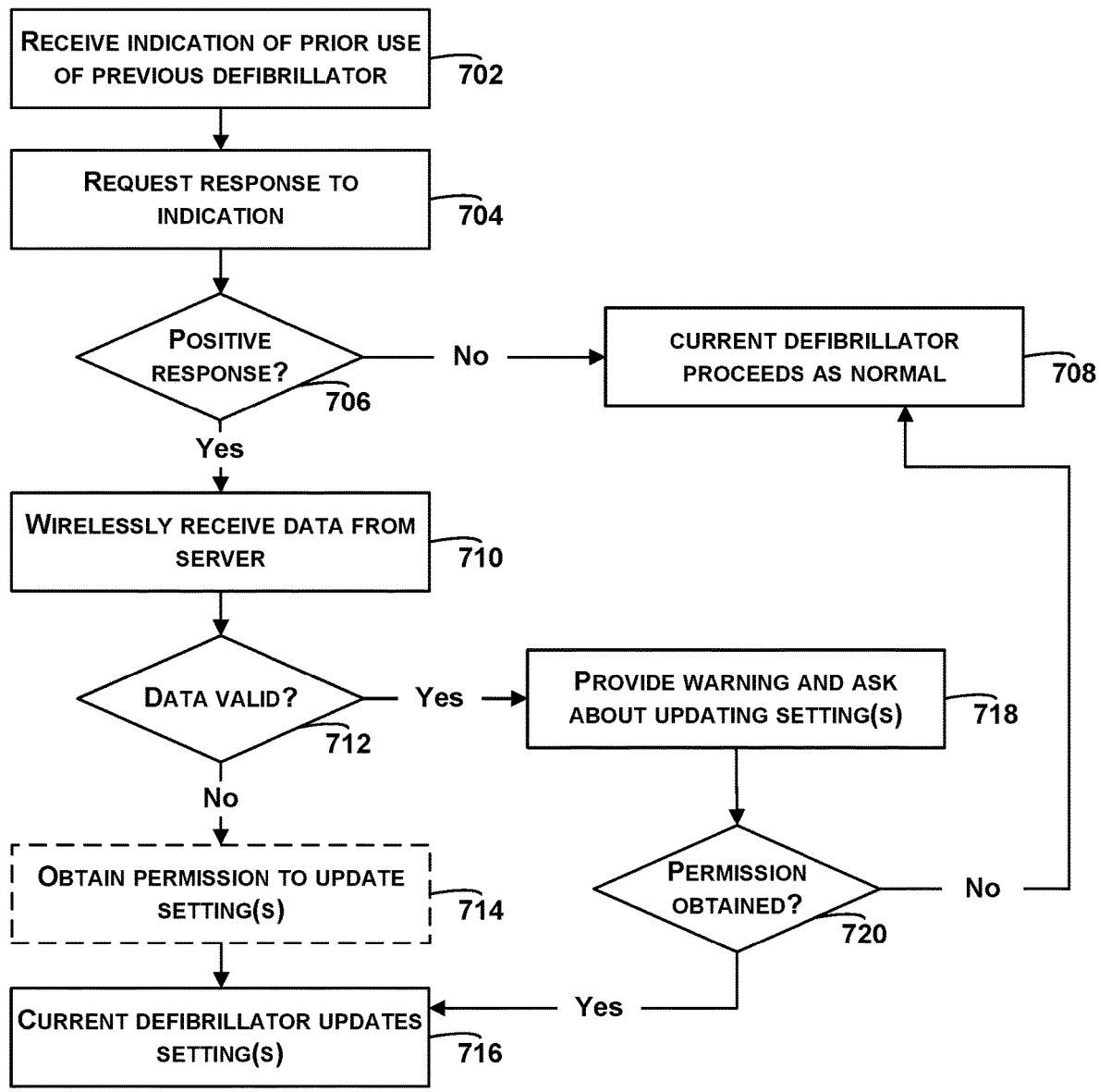
FIG. 7 is still another block diagram illustrating example acts that can be carried out in conjunction with use of a defibrillator, according to an example implementation.

FIGS. 5-7 are block diagrams illustrating sets of acts that can be carried out in conjunction with use of a current defibrillator during a patient care event. In some examples, the current defibrillator can be an AED, such as AED 200 of FIG. 2. In other examples, the current defibrillator can be a monitor defibrillator, such as monitor defibrillator 300 of FIG. 3.

As shown in FIG. 5, in one example, at block 502, a therapy cable is plugged into the current defibrillator. The therapy cable can be a therapy cable of the previous defibrillator that was used to deliver a previous shock. Further, at block 504, the current defibrillator queries the therapy cable so as to determine whether the therapy cable includes a memory. The memory can be the memory 220 of FIG. 2 or the memory 320 of FIG. 3, for instance. A processor of the current defibrillator can query the therapy cable by sending a read command via one or more of the pins of a connector of the therapy cable. If the therapy cable includes a memory, the processor can access a portion of the data as a result of the read command.

As further shown in FIG. 5, at block 506, a processor of the current defibrillator then makes a decision based on whether or not the therapy cable includes a memory. The processor can make this decision based on a result of the read command, such as whether the processor is able to access data using the read command. If the processor determines that the therapy cable does not include a memory, then, at block 508, the current defibrillator proceeds as normal. Whereas, if the processor determines that the therapy cable includes a memory, then, at block 510, the processor retrieves data from the memory.

Retrieving the data from the memory can include checking if the data is valid. As one example, the processor can use a cyclic redundancy check to detect errors in the data. As another example, the processor can analyze a timestamp in the data to ensure that data in the cable corresponds to a current patient for which the current defibrillator is providing care. For instance, the processor of the defibrillator can determine whether a timestamp in the data, such as a timestamp associated with previous shock, is within a threshold time of a current time. The threshold time could be a number of minutes (e.g., four minutes, ten minutes, etc.).

As further shown in FIG. 5, at block 512, the processor of the current defibrillator then makes a decision based on whether or not the data is valid. If the processor determines that the data is valid, then, optionally, at block 514, the processor can obtain permission to update a setting of the current defibrillator using the data. Obtaining permission can involve providing an audible or visual prompt using a user interface of the current defibrillator. For instance, the current defibrillator can prompt a user to use an energy level of a previous shock delivered by the previous defibrillator to set the energy level of a subsequent shock.

After providing the prompt, the current defibrillator can obtain, via the user interface, an instruction to use the data to update a setting of the current defibrillator. Further, at block 516, the processor of the current defibrillator can update at least one setting of the current defibrillator based on the data.

The processor of the current defibrillator can use the data to update a setting of the current defibrillator in various ways. As one example, the processor can set the energy level for a subsequent shock based on data indicative of an energy level of a previous shock. For instance, the processor can increase the energy level from the energy level of the previous shock to a next energy level in an energy level sequence. The energy level sequence could be 200 Joules, 300 Joules, and 360 Joules. With this configuration, based on data indicating that an energy level of a previous shock was 200 Joules, the processor can set the energy level for the subsequent shock to 300 Joules. The decision to increase the energy level could be further based on a determination that the energy level of the previous shock was not the maximum energy level in the energy level sequence. In some examples, the processor of the current defibrillator can also cause the user interface of the current defibrillator to provide an indication of the energy level of the previous shock.

As another example, the processor can set the energy level for a subsequent shock based on data indicating that ROSC was achieved after delivering the previous shock. For instance, the processor can set the energy level of the previous shock as the energy level for the subsequent shock based on the data indicating that ROSC was achieved. Alternatively, the processor can increase the energy level even though the data indicates that ROSC was achieved. The manner in which the processor selects the energy level for the subsequent shock when data indicates that ROSC was achieved could be a configurable option. For instance, an operator of the current defibrillator could choose between having the processor keep the energy level the same or having the processor increase the energy level when data indicates that ROSC was achieved. In some examples, the processor of the current defibrillator can also cause the user interface of the current defibrillator to provide an indication that ROSC was achieved after delivering the previous shock.

As another example, the processor can set the energy level for a subsequent shock based on data indicative of a fibrillation type. The data indicative of the fibrillation type can qualify whether or not the patient's rhythm reverted to a life-sustaining rhythm after delivery of the previous shock. For instance, the data indicative of fibrillation type could qualify whether the VF observed by the previous defibrillator and leading up to the previous shock was refractory VF or recurrent VF. If the data indicative of the fibrillation type is indicative of refractory VF, the processor can increase the energy level from the energy level of the previous shock to a next energy level in an energy level sequence. On the other hand, if the data is indicative of recurrent VF, the processor can set the energy level of the previous shock as the energy level for the subsequent shock. Maintaining the same energy level may be preferred in such a scenario as the previous energy level was demonstrated to be successful. By maintaining the same energy level, this decreases the change of injury due to cardiomyocytes. In other instances, the processor can increase the energy level even though the data indicates the occurrence of recurrent VF. Again, the configuration of the current defibrillator could dictate the action that the processor takes with respect to the energy level. In some examples, the processor of the current defibrillator can also cause the user interface of the current defibrillator to provide an indication of the fibrillation type.

As another example, the processor can set the energy level for a subsequent shock based on data indicative of whether a post-shock rhythm detected by the previous defibrillator was shockable or non-shockable. For instance, if the data indicates that a post-shock detected rhythm was shockable, the processor can increase the energy level from the energy level of the previous shock to a next energy level in an energy level sequence. On the other hand, if the data indicates that a post-shock detected rhythm was non-shockable, the processor can set the energy level of the previous shock as the energy level for the subsequent shock. Again, the configuration of the current defibrillator could dictate the action that the processor takes with respect to the energy level. In some examples, the processor of the current defibrillator can also cause the user interface of the current defibrillator to provide an indication of whether the post-shock detected rhythm was shockable or non-shockable.

As further shown in FIG. 5, if the processer determines that the data is not valid at block 512 (e.g., due to errors in the data or an inconsistency between the timestamp and a current time), then, at block 518, the processor can cause a user interface of the current defibrillator to provide a warning regarding the validity of the data and request permission to update a setting of the current defibrillator using the data despite the error. Requesting permission can involve providing an audible or visual prompt using a user interface of the current defibrillator. Subsequently, at block 520, the processor can make a decision based on whether or not permission is obtained. If the current defibrillator obtains permission, then, as described above, the processor of the current defibrillator can update at least one setting of the current defibrillator based on the data. Whereas, if the current defibrillator does not obtain permission, the current defibrillator proceeds as normal.

In some examples, the processor of the current defibrillator can also cause the user interface of the current defibrillator to display portions of the data retrieved from the memory or information derived from the data. As one example, the processor can cause the user interface to display a timer indicating a remaining amount of time until the time to deliver the subsequent shock. This timer can be derived from a timestamp associated with the previous shock. As another example, the processor can cause the user interface to display an identification of the previous defibrillator (e.g., a model number) and a number of shocks delivered to the patient using the previous defibrillator. As another example, the processor can cause the user interface to display an indication of the coarseness of the VF waveform measured by the previous defibrillator. As still another example, the processor can cause the user interface to display an initial rhythm measured by the previous defibrillator and, optionally, an algorithm used to measure the initial rhythm.

As still another example, the processor can cause the user interface to display an indication of an error code associated with the previous shock. As still another example, the processor can cause the user interface to display an indication of whether or not CPR was performed on the patient or an indication of whether or not the previous defibrillator advised a user to continue CPR after the previous shock was delivered.

The processor of the current defibrillator can also write any of the data that is obtained from the memory of the therapy cable to a patient record. Further, the current defibrillator can transmit the patient record to another device using the wireless communication interface.

In another example, as shown in FIG. 6, optionally, at block 602, a therapy cable is plugged into the current defibrillator. The therapy cable can be a therapy cable of the previous defibrillator that was used to deliver a previous shock. Further, at block 604, the current defibrillator searches for nearby defibrillators. The searching can vary depending on the wireless communication protocol utilized by the current defibrillator. As one example, the current defibrillator could perform a search for nearby devices that are broadcasting a tag which identifies the device as a defibrillator, such as nearby devices that are broadcasting a tag in accordance with a Bluetooth protocol. As another example, the current defibrillator could search for a nearby NFC device. Upon determining that another defibrillator is within wireless range of the current defibrillator, then, based on the determining, the current defibrillator can established a wireless communication link with the other defibrillator.

As further shown in FIG. 6, at block 606, a processor of the current defibrillator then makes a decision based on whether or not the current defibrillator identifies and establishes a valid connection with another defibrillator. As part of the decision at block 606, the processor of the current defibrillator can evaluate a geographic location of the other defibrillator. For instance, the processor can determine that the other defibrillator is located within a threshold distance of a geographic location of the current defibrillator. Based on the determining that the other defibrillator is located within a threshold distance of the geographic location of the current defibrillator, the processor can determine that a valid connection is established.

If the processor determines that a valid connection with another defibrillator has not been established, then, at block 608, the current defibrillator proceeds as normal. Whereas, if the processor determines that a valid connection with another defibrillator has been established, then, at block 610, the current defibrillator wirelessly receives data from the other defibrillator.

Wirelessly receiving the data can include checking if the data is valid. As one example, the processor can use a cyclic redundancy check to detect errors in the data. As another example, the processor can analyze a timestamp in the data to ensure that data in the cable corresponds to a current patient for which the current defibrillator is providing care. For instance, the processor of the defibrillator can determine whether a timestamp in the data, such as a timestamp associated with previous shock, is within a threshold time of a current time. The threshold time could be a number of minutes (e.g., four minutes, ten minutes, etc.). In a scenario in which a therapy cable of another defibrillator is plugged into the current defibrillator, the processor can compare a first unique identifier in the data with a second unique identifier that is retrieved from a memory embedded within the therapy cable. To check the validity of the data, the processor can therefore determine whether the first unique identifier and the second unique identifier are the same.

In some examples, wirelessly receiving data from the other defibrillator can include wirelessly receiving data from a wireless communication interface embedded within a therapy cable of the other defibrillator. This wireless reception of data can occur while the therapy cable of the other defibrillator is plugged into the other defibrillator, while the therapy cable of the other defibrillator is plugged into the current defibrillator, or while the therapy cable of the other defibrillator is not plugged into a defibrillator.

As further shown in FIG. 6, at block 612, the processor of the current defibrillator then makes a decision based on whether or not the data is valid. If the processor determines that the data is valid, then, optionally, at block 614, the processor can obtain permission to update a setting of the current defibrillator using the data. Obtaining permission can involve providing an audible or visual prompt using a user interface of the current defibrillator. For instance, the current defibrillator can prompt a user to use an energy level of a previous shock delivered by the previous defibrillator to set the energy level of a subsequent shock.

After providing the prompt, the current defibrillator can obtain, via the user interface, an instruction to use the data to update a setting of the current defibrillator. Further, at block 616, the processor of the current defibrillator can update at least one setting of the current defibrillator based on the data.

The processor of the current defibrillator can use the data to update a setting of the current defibrillator in various ways. As one example, the processor can set the energy level for a subsequent shock based on data indicative of an energy level of a previous shock. For instance, the processor can increase the energy level from the energy level of the previous shock to a next energy level in an energy level sequence. The energy level sequence could be 200 Joules, 300 Joules, and 360 Joules. With this configuration, based on data indicating that an energy level of a previous shock was 200 Joules, the processor can set the energy level for the subsequent shock to 300 Joules. The decision to increase the energy level could be further based on a determination that the energy level of the previous shock was not the maximum energy level in the energy level sequence. In some examples, the processor of the current defibrillator can also cause the user interface of the current defibrillator to provide an indication of the energy level of the previous shock.

As another example, the processor can set the energy level for a subsequent shock based on data indicating that ROSC was achieved after delivering the previous shock. For instance, the processor can set the energy level of the previous shock as the energy level for the subsequent shock based on the data indicating that ROSC was achieved. Alternatively, the processor can increase the energy level even though the data indicates that ROSC was achieved. The manner in which the processor selects the energy level for the subsequent shock when data indicated that ROSC was achieved could be a configurable option. For instance, an operator of the current defibrillator could choose between having the processor keep the energy level the same or having the processor increase the energy level when data indicates that ROSC was achieved. In some examples, the processor of the current defibrillator can also cause the user interface of the current defibrillator to provide an indication that ROSC was achieved after delivering the previous shock.

As another example, the processor can set the energy level for a subsequent shock based on data indicative of a fibrillation type. The data indicative of the fibrillation type can qualify whether or not the patient's rhythm reverted to a life-sustaining rhythm after delivery of the previous shock. VF can be qualified as either refractory VF or recurrent VF. Refractory VF refers to VF that persists despite shock delivery. This is in contrast to recurrent VF, which is VF that re-appears after it had previously been terminated. The data indicative of fibrillation type could qualify whether the VF observed by the previous defibrillator and leading up to the previous shock was refractory VF or recurrent VF. If the data indicative of the fibrillation type is indicative of refractory VF, the processor can increase the energy level from the energy level of the previous shock to a next energy level in an energy level sequence. On the other hand, if the data is indicative of recurrent VF, the processor can set the energy level of the previous shock as the energy level for the subsequent shock based on Maintaining the same energy level may be preferred in such a scenario as the previous energy level was demonstrated to be successful. By maintaining the same energy level, this decreases the change of injury due to cardiomyocytes. In other instances, the processor can increase the energy level even though the data indicates the occurrence of recurrent VF. Again, the configuration of the current defibrillator could dictate the action that the processor takes with respect to the energy level. In some examples, the processor of the current defibrillator can also cause the user interface of the current defibrillator to provide an indication of the fibrillation type.

As another example, the processor can set the energy level for a subsequent shock based on data indicative of whether a post-shock rhythm detected by the previous defibrillator was shockable or non-shockable. For instance, if the data indicates that a post-shock detected rhythm was shockable, the processor can increase the energy level from the energy level of the previous shock to a next energy level in an energy level sequence. On the other hand, if the data indicates that a post-shock detected rhythm was non-shockable, the processor can set the energy level of the previous shock as the energy level for the subsequent shock. Again, the configuration of the current defibrillator could dictate the action that the processor takes with respect to the energy level. In some examples, the processor of the current defibrillator can also cause the user interface of the current defibrillator to provide an indication of whether the post-shock detected rhythm was shockable or non-shockable.

As further shown in FIG. 6, if the processer determines that the data is not valid at block 612 (e.g., due to errors in the data or an inconsistency between the timestamp and a current time), then, at block 618, the processor can cause a user interface of the current defibrillator to provide a warning regarding the validity of the data and request permission to update a setting of the current defibrillator using the data despite the error. Requesting permission can involve providing an audible or visual prompt using a user interface of the current defibrillator. Subsequently, at block 620, the processor can make a decision based on whether or not permission is obtained. If the current defibrillator obtains permission, then, as described above, the processor of the current defibrillator can update at least one setting of the current defibrillator based on the data. Whereas, if the current defibrillator does not obtain permission, the current defibrillator proceeds as normal.

In some examples, the processor of the current defibrillator can also cause the user interface of the current defibrillator to display portions of the wirelessly received data or information derived from the wirelessly received data. As one example, the processor can cause the user interface to display a timer indicating a remaining amount of time until the time to deliver the subsequent shock. This timer can be derived from a timestamp associated with the previous shock. As another example, the processor can cause the user interface to display an identification of the previous defibrillator (e.g., a model number) and a number of shocks delivered to the patient using the previous defibrillator. As another example, the processor can cause the user interface to display an indication of the coarseness of the VF waveform measured by the previous defibrillator. As still another example, the processor can cause the user interface to display an initial rhythm measured by the previous defibrillator and, optionally, an algorithm used to measure the initial rhythm.

As still another example, the processor can cause the user interface to display an indication of an error code associated with the previous shock. As still another example, the processor can cause the user interface to display an indication of whether or not CPR was performed on the patient or an indication of whether or not the previous defibrillator advised a user to continue CPR after the previous shock was delivered.

The processor of the current defibrillator can also write any of the wirelessly received data to a patient record.

Further, the current defibrillator can transmit the patient record to another device using the wireless communication interface.

In another example, as shown in FIG. 7, at block 702, the current defibrillator can receive an indication of a prior use of another defibrillator. For example, the current defibrillator can wirelessly receive from a server an indication that another defibrillator was recently used within a threshold distance of a geographic location of the current defibrillator. In some instances, an operator of the current defibrillator or a bystander can trigger the server to provide the indication using a user interface of the other defibrillator (e.g., by holding down a button on a user interface of the other defibrillator). Providing the input can cause the other defibrillator to send a message to the server. In response to receiving the message, the server can then determine that the current defibrillator is within a threshold distance of a geographic location of the other defibrillator, and provide the indication to the current defibrillator. In other instances, the presence of the current defibrillator within a threshold distance of a geographic location where the other defibrillator was recently used can trigger the sending of the indication by the server.

At block 704, the current defibrillator can request a response to the indication. For instance, in response to receiving the indication, a processor of the current defibrillator can cause a user interface of the current defibrillator to present a visual or audible prompt. The prompt can indicate that another defibrillator was recently used nearby, and ask an operator of the current defibrillator to confirm that the other defibrillator was used to treat the same patient that the operator is currently providing care for. By way of example, the indication received at block 702 can include a location-specific prompt that a user of the current defibrillator can respond to. For instance, the indication can be a question such as "Are you located at an ABC Hamburger Shop in downtown Seattle?" The processor of the current defibrillator can cause the user interface to present the prompt (e.g., visually and/or audibly).

After requesting the response, the current defibrillator can obtain a response via the user interface, and provide the response to the server. The response can be a positive response (e.g., confirmation of the prior use and request to receive data), or a negative response (e.g., election to ignore the prior use and not receive data).

As further shown in FIG. 7, at block 706, the set of acts then varies based on the response. If the response is a negative response, then, at block 708, the current defibrillator proceeds as normal. Whereas, if the response is a positive response, then, at block 710, the current defibrillator wirelessly receives data from the server.

Wirelessly receiving the data can include checking if the data is valid. As one example, the processor can use a cyclic redundancy check to detect errors in the data. As another example, the processor can analyze a timestamp in the data to ensure that data in the cable corresponds to a current patient for which the current defibrillator is providing care. For instance, the processor of the defibrillator can determine whether a timestamp in the data, such as a timestamp associated with previous shock, is within a threshold time of a current time. The threshold time could be a number of minutes (e.g., four minutes, ten minutes, etc.). In a scenario in which a therapy cable of another defibrillator is plugged into the current defibrillator, the processor can compare a first unique identifier in the data with a second unique identifier that is retrieved from a memory embedded within the therapy cable. To check the validity of the data, the processor can therefore determine whether the first unique identifier and the second unique identifier are the same.

As further shown in FIG. 7, at block 712, the processor of the current defibrillator then makes a decision based on whether or not the data is valid. If the processor determines that the data is valid, then, optionally, at block 714, the processor can obtain permission to update a setting of the current defibrillator using the data. Obtaining permission can involve providing an audible or visual prompt using a user interface of the current defibrillator. For instance, the current defibrillator can prompt a user to use an energy level of a previous shock delivered by the previous defibrillator to set the energy level of a subsequent shock.

After providing the prompt, the current defibrillator can obtain, via the user interface, an instruction to use the data to update a setting of the current defibrillator. Further, at block 616, the processor of the current defibrillator can update at least one setting of the current defibrillator based on the data.

The processor of the current defibrillator can use the data to update a setting of the current defibrillator in various ways. As one example, the processor can set the energy level for a subsequent shock based on data indicative of an energy level of a previous shock. For instance, the processor can increase the energy level from the energy level of the previous shock to a next energy level in an energy level sequence. The energy level sequence could be 200 Joules, 300 Joules, and 360 Joules. With this configuration, based on data indicating that an energy level of a previous shock was 200 Joules, the processor can set the energy level for the subsequent shock to 300 Joules. The decision to increase the energy level could be further based on a determination that the energy level of the previous shock was not the maximum energy level in the energy level sequence. In some examples, the processor of the current defibrillator can also cause the user interface of the current defibrillator to provide an indication of the energy level of the previous shock.

As another example, the processor can set the energy level for a subsequent shock based on data indicating that ROSC was achieved after delivering the previous shock. For instance, the processor can set the energy level of the previous shock as the energy level for the subsequent shock based on the data indicating that ROSC was achieved. Alternatively, the processor can increase the energy level even though the data indicates that ROSC was achieved. The manner in which the processor selects the energy level for the subsequent shock when data indicated that ROSC was achieved could be a configurable option. For instance, an operator of the current defibrillator could choose between having the processor keep the energy level the same or having the processor increase the energy level when data indicates that ROSC was achieved. In some examples, the processor of the current defibrillator can also cause the user interface of the current defibrillator to provide an indication that ROSC was achieved after delivering the previous shock.

As another example, the processor can set the energy level for a subsequent shock based on data indicative of a fibrillation type. The data indicative of the fibrillation type can qualify whether or not the patient's rhythm reverted to a life-sustaining rhythm after delivery of the previous shock. VF can be qualified as either refractory VF or recurrent VF. Refractory VF refers to VF that persists despite shock delivery. This is in contrast to recurrent VF, which is VF that re-appears after it had previously been terminated. The data indicative of fibrillation type could qualify whether the VF observed by the previous defibrillator and leading up to the previous shock was refractory VF or recurrent VF. If the data indicative of the fibrillation type is indicative of refractory VF, the processor can increase the energy level from the energy level of the previous shock to a next energy level in an energy level sequence. On the other hand, if the data is indicative of recurrent VF, the processor can set the energy level of the previous shock as the energy level for the subsequent shock based on Maintaining the same energy level may be preferred in such a scenario as the previous energy level was demonstrated to be successful. By maintaining the same energy level, this decreases the change of injury due to cardiomyocytes. In other instances, the processor can increase the energy level even though the data indicates the occurrence of recurrent VF. Again, the configuration of the current defibrillator could dictate the action that the processor takes with respect to the energy level. In some examples, the processor of the current defibrillator can also cause the user interface of the current defibrillator to provide an indication of the fibrillation type.

As another example, the processor can set the energy level for a subsequent shock based on data indicative of whether a post-shock rhythm detected by the previous defibrillator was shockable or non-shockable. For instance, if the data indicates that a post-shock detected rhythm was shockable, the processor can increase the energy level from the energy level of the previous shock to a next energy level in an energy level sequence. On the other hand, if the data indicates that a post-shock detected rhythm was non-shockable, the processor can set the energy level of the previous shock as the energy level for the subsequent shock. Again, the configuration of the current defibrillator could dictate the action that the processor takes with respect to the energy level. In some examples, the processor of the current defibrillator can also cause the user interface of the current defibrillator to provide an indication of whether the post-shock detected rhythm was shockable or non-shockable.

As further shown in FIG. 7, if the processer determines that the data is not valid at block 712 (e.g., due to errors in the data or an inconsistency between the timestamp and a current time), then, at block 718, the processor can cause a user interface of the current defibrillator to provide a warning regarding the validity of the data and request permission to update a setting of the current defibrillator using the data despite the error. Requesting permission can involve providing an audible or visual prompt using a user interface of the current defibrillator. Subsequently, at block 720, the processor can make a decision based on whether or not permission is obtained. If the current defibrillator obtains permission, then, as described above, the processor of the current defibrillator can update at least one setting of the current defibrillator based on the data. Whereas, if the current defibrillator does not obtain permission, the current defibrillator proceeds as normal.

In some examples, the processor of the current defibrillator can also cause the user interface of the current defibrillator to display portions of the wirelessly received data or information derived from the wirelessly received data. As one example, the processor can cause the user interface to display a timer indicating a remaining amount of time until the time to deliver the subsequent shock. This timer can be derived from a timestamp associated with the previous shock. As another example, the processor can cause the user interface to display an identification of the previous defibrillator (e.g., a model number) and a number of shocks delivered to the patient using the previous defibrillator. As another example, the processor can cause the user interface to display an indication of the coarseness of the VF waveform measured by the previous defibrillator. As still another example, the processor can cause the user interface to display an initial rhythm measured by the previous defibrillator and, optionally, an algorithm used to measure the initial rhythm.

As still another example, the processor can cause the user interface to display an indication of an error code associated with the previous shock. As still another example, the processor can cause the user interface to display an indication of whether or not CPR was performed on the patient or an indication of whether or not the previous defibrillator advised a user to continue CPR after the previous shock was delivered.

The processor of the current defibrillator can also write any of the wirelessly received data to a patient record. Further, the current defibrillator can transmit the patient record to another device using the wireless communication interface.

Figure 8:
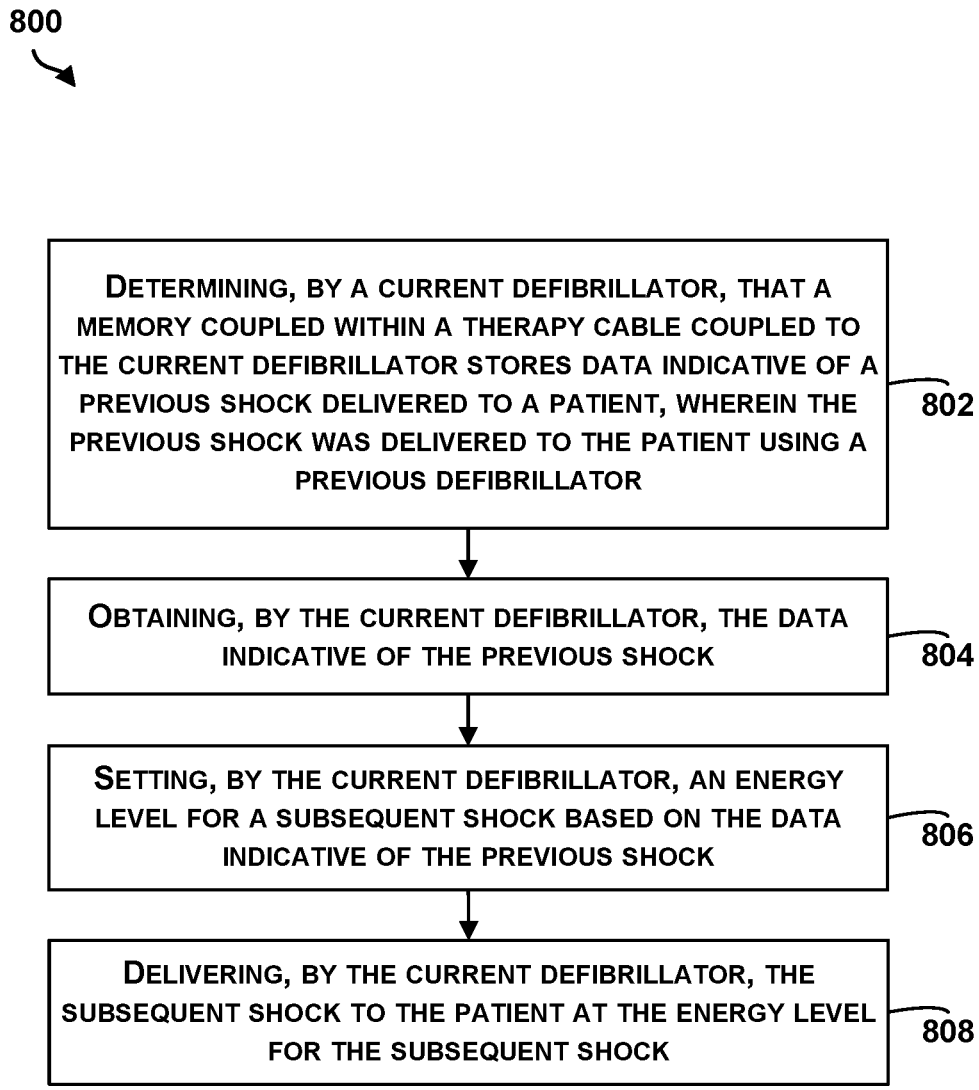
FIG. 8 shows a flowchart of an example of a method performed by a defibrillator, according to an example implementation.

FIG. 8 shows a flowchart of an example of a method 800 performed by a defibrillator, according to an example implementation. Method 800 shown in FIG. 8 presents an example of a method that could be performed by a defibrillator, such as the AED 200 shown in FIG. 2 or with the monitor defibrillator 300 shown in FIG. 3, for example. Further, devices or systems may be used or configured to perform logical functions presented in FIG. 8. In some instances, components of the devices and/or systems may be configured to perform the functions such that the components are actually configured and structured (with hardware and/or software) to enable such performance. In other examples, components of the devices and/or systems may be arranged to be adapted to, capable of, or suited for performing the functions, such as when operated in a specific manner. Method 800 may include one or more operations, functions, or actions as illustrated by one or more of blocks 802-808. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

It should be understood that for this and other processes and methods disclosed herein, flowcharts show functionality and operation of one possible implementation of present examples. In this regard, each block or portions of each block may represent a module, a segment, or a portion of program code, which includes one or more instructions executable by a processor for implementing specific logical functions or steps in the process. The program code may be stored on any type of computer readable medium or data storage, for example, such as a storage device including a disk or hard drive. Further, the program code can be encoded on a computer-readable storage media in a machine-readable format, or on other non-transitory media or articles of manufacture. The computer readable medium may include non-transitory computer readable medium or memory, for example, such as computer-readable media that stores data for short periods of time like register memory, processor cache and Random Access Memory (RAM). The computer readable medium may also include non-transitory media, such as secondary or persistent long-term storage, like read only memory (ROM), optical or magnetic disks, compact-disc read only memory (CD-ROM), for example. The computer readable media may also be any other volatile or non-volatile storage systems. The computer readable medium may be considered a tangible computer readable storage medium, for example.

In addition, each block or portions of each block in FIG. 8, and within other processes and methods disclosed herein, may represent circuitry that is wired to perform the specific logical functions in the process. Alternative implementations are included within the scope of the examples of the present disclosure in which functions may be executed out of order from that shown or discussed, including substantially concurrent or in reverse order, depending on the functionality involved, as would be understood by those reasonably skilled in the art.

At block 802, method 800 includes determining, by a current defibrillator, that a memory embedded within a therapy cable coupled to the current defibrillator stores data indicative of a previous shock delivered to a patient, with the previous shock being delivered to the patient using a previous defibrillator. In some examples, the therapy cable is a therapy cable of the previous defibrillator.

At block 804, method 800 includes obtaining, by the current defibrillator, the data indicative of the previous shock. In some examples, the current defibrillator is a monitor defibrillator, and the previous defibrillator is an AED At block 806, method 800 includes setting, by the current defibrillator, an energy level for a subsequent shock based on the data indicative of the previous shock. In one example, the data indicative of the previous shock includes an energy level of the previous shock, and setting the energy level for the subsequent shock includes setting the energy level for the subsequent shock based on the energy level of the previous shock. For instance, setting the energy level for the subsequent shock can include increasing the energy level of the previous shock so as to obtain the energy level of the subsequent shock.

In another example, the memory stores data indicating that return of ROSC was achieved after delivering the previous shock, and setting the energy level includes setting the energy level of the previous shock as the energy level for the subsequent shock based on the data indicating that ROSC was achieved after delivering the previous shock. In another example, the memory stores data indicative of a fibrillation type, and setting the energy level for the subsequent shock includes setting the energy level of the previous shock as the energy level for the subsequent shock based on the fibrillation type. In another example, the memory stores data indicating that a post-shock detected rhythm was non-shockable, and setting the energy level for the subsequent shock includes setting the energy level of the previous shock as the energy level for the subsequent shock based on the data indicating that a post-shock detected rhythm was non-shockable.

In yet another example, the data indicative of the previous shock includes a timestamp associated with the previous shock, and method 800 also includes determining that the timestamp corresponds to a time that is within a threshold time of a current time. Further, the setting of the energy level of the subsequent shock is then based on the determining that the timestamp corresponds to the time that is within the threshold time of the current time.

In yet another example, the data indicative of the previous shock includes a timestamp associated with the previous shock, and method 800 also includes (i) determining, based on the timestamp, a time to deliver the subsequent shock and (ii) displaying, by the current defibrillator, a timer indicating a remaining amount of time until the time to deliver the subsequent shock.

At block 808, method 800 includes delivering, by the current defibrillator, the subsequent shock to the patient at the energy level for the subsequent shock.

In some examples, method 800 also includes obtaining, by the current defibrillator, an instruction to use the data indicative of the previous shock to set the energy level of the subsequent shock. Further, the setting of the energy level of the subsequent shock is then based on the obtaining the instruction.

In some examples, method 800 also includes storing, by the current defibrillator, at least a portion of the data indicative of the previous shock in a patient record of the patient. Further, the data indicative of the previous shock includes an identification of the previous defibrillator and a number of shocks delivered to the patient using the previous defibrillator. The identification includes a model number or serial number of the previous defibrillator.

In some examples, the memory stores data indicative of a coarseness of a VF waveform measured by the previous defibrillator, and method 800 further includes providing, by the current defibrillator, an indication of the coarseness of the VF waveform.

In some examples, the memory stores data indicative of an initial rhythm measured by the previous defibrillator, and method 800 further includes providing, by the current defibrillator, an indication of the initial rhythm measured by the previous defibrillator. The memory also stores data indicative of an algorithm used to measure the initial rhythm.

In some examples, the memory stores data indicative of an error code associated with the previous shock, and method 800 also includes providing, by the current defibrillator, an indication of the error code.

In some examples, the memory stores one or both of: data indicative of whether or not CPR was performed on the patient; and data indicative of whether or not the previous defibrillator advised a user to continue CPR after the previous shock was delivered.

Figure 9:
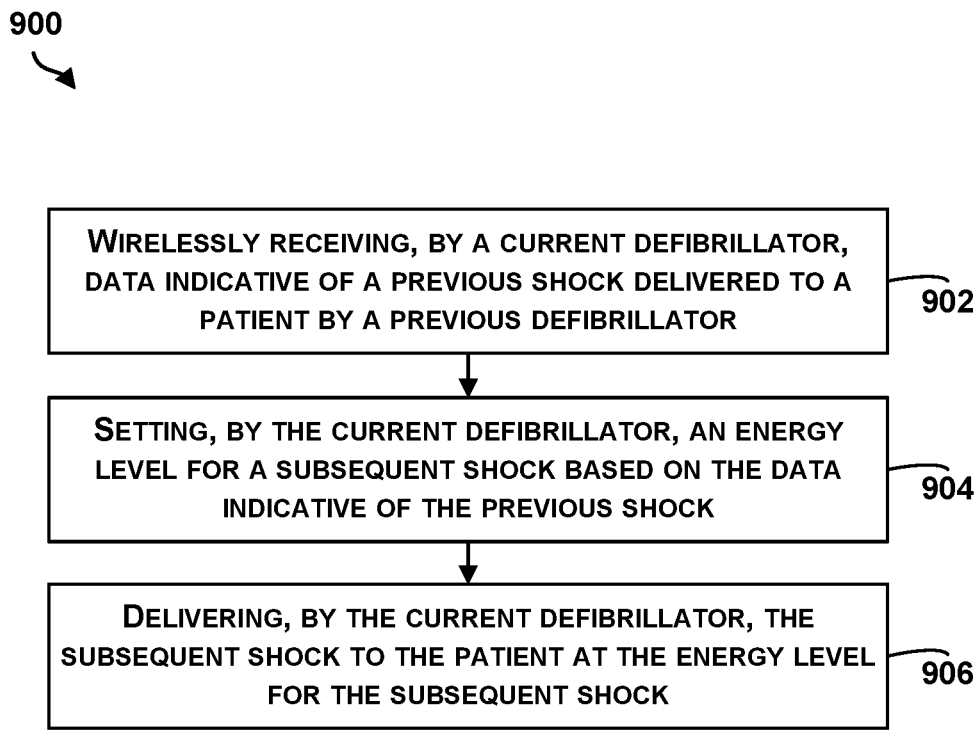
FIG. 9 shows a flowchart of another example of a method performed by a defibrillator, according to an example implementation.

FIG. 9 shows a flowchart of another example of a method performed by a defibrillator. Method 900 shown in FIG. 9 presents an example of a method that could be performed by AED 200 of FIG. 2 or monitor defibrillator 300 of FIG. 3, for example. Further, devices or systems may be used or configured to perform logical functions presented in FIG. 9.

At block 902, method 900 includes wirelessly receiving, by a current defibrillator, data indicative of a previous shock delivered to a patient by a previous defibrillator. In some examples, the current defibrillator is a monitor defibrillator, and the previous defibrillator is an AED In one example, wirelessly receiving the data indicative of the previous shock includes wirelessly receiving the data indicative of the previous shock from a server. Further, method 900 also includes sending, by the current defibrillator, a geographic location of the current defibrillator to the server prior to wirelessly receiving the data indicative of the previous shock. The previous shock was delivered to the patient within a threshold distance of the geographic location of the current defibrillator.

At block 904, method 900 includes setting, by the current defibrillator, an energy level for a subsequent shock based on the data indicative of the previous shock.

In one example, wirelessly receiving the data indicative of the previous shock includes wirelessly receiving the data indicative of the previous shock from the previous defibrillator. Further, method 900 also includes: (i) determining, by the current defibrillator, that the previous defibrillator is within wireless range of the current defibrillator; and (ii) based on the determining, establishing, by the current defibrillator, a wireless communication link with the previous defibrillator. Additionally or alternatively, method 900 also includes determining, by the current defibrillator, that the previous defibrillator is located within a threshold distance of a geographic location of the current defibrillator. Further, the setting the energy level is then based on the determining that the previous defibrillator is located within the threshold distance of the geographic location of the current defibrillator.

In some examples, the data indicative of the previous shock includes a first unique identifier. In these examples, method 900 also includes: (i) obtaining, by the current defibrillator, a second unique identifier from a memory embedded within a therapy cable coupled to the current defibrillator; and (ii) determining, by the current defibrillator, that the first unique identifier and the second unique identifier are the same. Further, the setting the energy level is based on the determining that the first unique identifier and the second unique identifier are the same.

In some examples, the data indicative of the previous shock includes an energy level of the previous shock, and setting the energy level for the subsequent shock includes setting the energy level for the subsequent shock based on the energy level of the previous shock. For instance, setting the energy level for the subsequent shock can include increasing the energy level of the previous shock so as to obtain the energy level of the subsequent shock.

In one example, the memory stores data indicating that return of ROSC was achieved after delivering the previous shock, and setting the energy level includes setting the energy level of the previous shock as the energy level for the subsequent shock based on the data indicating that ROSC was achieved after delivering the previous shock. In another example, the memory stores data indicative of a fibrillation type, and setting the energy level for the subsequent shock includes setting the energy level of the previous shock as the energy level for the subsequent shock based on the fibrillation type. In another example, the memory stores data indicating that a post-shock detected rhythm was non-shockable, and setting the energy level for the subsequent shock includes setting the energy level of the previous shock as the energy level for the subsequent shock based on the data indicating that a post-shock detected rhythm was non-shockable.

In another example, the data indicative of the previous shock includes a timestamp associated with the previous shock, and method 900 also includes determining that the timestamp corresponds to a time that is within a threshold time of a current time. Further, the setting of the energy level of the subsequent shock is based on the determining that the timestamp corresponds to the time that is within the threshold time of the current time.

In yet another example, the data indicative of the previous shock includes a timestamp associated with the previous shock, and method 900 also includes (i) determining, based on the timestamp, a time to deliver the subsequent shock and (ii) displaying, by the current defibrillator, a timer indicating a remaining amount of time until the time to deliver the subsequent shock.

At block 906, method 900 includes delivering, by the current defibrillator, the subsequent shock to the patient at the energy level for the subsequent shock.

In some examples, method 900 also includes obtaining, by the current defibrillator, an instruction to use the data indicative of the previous shock to set the energy level of the subsequent shock. Further, the setting of the energy level of the subsequent shock is then based on the obtaining the instruction.

In some examples, method 900 also includes storing, by the current defibrillator, at least a portion of the data indicative of the previous shock in a patient record of the patient. Further, the data indicative of the previous shock includes an identification of the previous defibrillator and a number of shocks delivered to the patient using the previous defibrillator. The identification includes a model number or serial number of the previous defibrillator.

In some examples, method 900 also includes wirelessly receiving data indicative of a coarseness of a VF waveform measured by the previous defibrillator, and providing, by the current defibrillator, an indication of the coarseness of the VF waveform.

In some examples, method 900 also includes wirelessly receiving data indicative of an initial rhythm measured by the previous defibrillator, and providing, by the current defibrillator, an indication of the initial rhythm measured by the previous defibrillator. Method 900 can further include wirelessly receiving data indicative of an algorithm used to measure the initial rhythm.

In some examples, method 900 also includes wirelessly receiving data indicative of an error code associated with the previous shock, and providing, by the current defibrillator, an indication of the error code.

In some examples, method 900 also includes wirelessly receiving one or both of: data indicative of whether or not CPR was performed on the patient; and data indicative of whether or not the previous defibrillator advised a user to continue CPR after the previous shock was delivered.

The systems and methods described herein are very beneficial for providing better patient care during a cardiac event. When a patient undergoes a cardiac arrest, it is common for nearby individuals to begin CPR and use a first defibrillator to provide care before an EMS crew arrives. When the EMS crew arrives, due to the chaos of the situation and the involvement of multiple bystanders, it is likely that the EMS crew may be unable to quickly and reliably determine how many shocks have been delivered to the patient. The EMS crew would prefer to know how many shocks were given to the patient, as well as any other data that was obtained by the first defibrillator (such as an energy level of a previous shock, whether ROSC was achieved, whether a post-shock non-shockable rhythm was detected, an initial heart rhythm, a fibrillation type, etc.). With this information, the EMS crew could update a second defibrillator that the EMS crew uses to provide care for the patient.

For instance, in many situations, it is advisable to increase the energy level for each shock that is delivered to a patient. Further, doing so can increase the chance of saving the patient's life. Providing data indicating an energy level of a previous shock from the previous defibrillator (i.e. the first defibrillator) to the current defibrillator (i.e. the second defibrillator) can allow the EMS crew that assumes care to increase the energy level of the next shock, rather than delivering another shock at the same energy level. Advantageously, the systems and methods described herein allow for seamless transfer of this information between the previous defibrillator and the current defibrillator, and can remove reliance on bystanders or the initial caregiver to relay information.

Further, implementations of this disclosure provide technological improvements that are particular to computer technology, for example, those concerning transfer of data between defibrillators. Computer-specific technological problems, such as how to securely and seamlessly transfer data between defibrillators, can be solved using technical solutions described herein.

By the term "substantially" and "about" used herein, it is meant that the recited characteristic, parameter, or value need not be achieved exactly, but that deviations or variations, including for example, tolerances, measurement error, measurement accuracy limitations and other factors known to skill in the art, may occur in amounts that do not preclude the effect the characteristic was intended to provide.

Different examples of the system(s), device(s), and method(s) disclosed herein include a variety of components, features, and functionalities. It should be understood that the various examples of the system(s), device(s), and method(s) disclosed herein may include any of the components, features, and functionalities of any of the other examples of the system(s), device(s), and method(s) disclosed herein in any combination or any sub-combination, and all of such possibilities are intended to be within the scope of the disclosure.

The description of the different advantageous arrangements has been presented for purposes of illustration and description, and is not intended to be exhaustive or limited to the examples in the form disclosed. Many modifications and variations will be apparent to those of ordinary skill in the art. Further, different advantageous examples may describe different advantages as compared to other advantageous examples. The example or examples selected are chosen and described in order to best explain the principles of the examples, the practical application, and to enable others of ordinary skill in the art to understand the disclosure for various examples with various modifications as are suited to the particular use contemplated.

What is claimed is:

1. A method comprising:
   receiving, by a current defibrillator, data indicative of a previous shock delivered to a patient by a previous defibrillator;
   determining, by the current defibrillator, that the previous defibrillator is located within a threshold distance of a geographic location of the current defibrillator;
   setting, by the current defibrillator, an energy level for a subsequent shock based on (i) the data indicative of the previous shock, and (ii) determining that the previous defibrillator is located within the threshold distance of the geographic location of the current defibrillator; and
   delivering, by the current defibrillator, the subsequent shock to the patient at the energy level for the subsequent shock.

2. The method of claim 1, wherein receiving the data indicative of the previous shock comprises wirelessly receiving the data indicative of the previous shock from a server.

3. The method of claim 2, further comprising sending, by the current defibrillator, a geographic location of the current defibrillator to the server prior to wirelessly receiving the data indicative of the previous shock, wherein the previous shock was delivered to the patient within a threshold distance of the geographic location of the current defibrillator.

4. The method of claim 1, wherein receiving the data indicative of the previous shock comprises wirelessly receiving the data indicative of the previous shock from the previous defibrillator.

5. The method of claim 4, further comprising:
   determining, by the current defibrillator, that the previous defibrillator is within wireless range of the current defibrillator; and based on the determining, establishing, by the current defibrillator, a wireless communication link with the previous defibrillator.

6. The method of claim 1, wherein the data indicative of the previous shock comprises a first unique identifier, wherein the method further comprises:
obtaining, by the current defibrillator, a second unique identifier from a memory embedded within a therapy cable coupled to the current defibrillator; and
determining, by the current defibrillator, that the first unique identifier and the second unique identifier are the same, and
wherein the setting the energy level is based on the determining that the first unique identifier and the second unique identifier are the same.

7. The method of claim 1, wherein the data indicative of the previous shock comprises an energy level of the previous shock, and wherein setting the energy level for the subsequent shock comprises setting the energy level for the subsequent shock based on the energy level of the previous shock.

8. The method of claim 7, further comprising receiving data indicating that return of spontaneous circulation (ROSC) was achieved after delivering the previous shock, wherein setting the energy level for the subsequent shock comprises setting the energy level of the previous shock as the energy level for the subsequent shock based on the data indicating that ROSC was achieved after delivering the previous shock.

9. The method of claim 7, further comprising receiving data indicative of a fibrillation type, and wherein setting the energy level for the subsequent shock comprises setting the energy level of the previous shock as the energy level for the subsequent shock based on the fibrillation type.

10. The method of claim 1, further comprising obtaining, by the current defibrillator, an instruction to use the data indicative of the previous shock to set the energy level of the subsequent shock, wherein the setting of the energy level of the subsequent shock is further based on the obtaining the instruction.

11. The method of claim 1, further comprising:
receiving data indicative of a coarseness of a ventricular fibrillation (VF) waveform measured by the previous defibrillator; and
providing, by the current defibrillator, an indication of the coarseness of the VF waveform.

12. The method of claim 1, further comprising:
receiving data indicative of an initial rhythm measured by the previous defibrillator; and
providing, by the current defibrillator, an indication of the initial rhythm measured by the previous defibrillator.

13. A method comprising:
receiving, by a current defibrillator, data indicative of a previous shock delivered to a patient by a previous defibrillator, wherein the data indicative of the previous shock comprises a timestamp associated with the previous shock;
determining that that the timestamp corresponds to a time that is within a threshold time of a current time;
setting, by the current defibrillator, an energy level for a subsequent shock based on (i) the data indicative of the previous shock, and (ii) determining that the timestamp corresponds to the time that is within the threshold time of the current time; and
delivering, by the current defibrillator, the subsequent shock to the patient at the energy level for the subsequent shock.

14. A method comprising:
receiving, by a current defibrillator, data indicative of a previous shock delivered to a patient by a previous defibrillator, wherein the data indicative of the previous shock comprises a timestamp associated with the previous shock;
determining, based on the timestamp associated with the previous shock, a time to deliver the subsequent shock;
setting, by the current defibrillator, an energy level for a subsequent shock based on the data indicative of the previous shock;
displaying, by the current defibrillator, a timer indicating a remaining amount of time until the time to deliver the subsequent shock; and
delivering, by the current defibrillator, the subsequent shock to the patient at the energy level for the subsequent shock.

15. A defibrillator comprising:
a non-transitory computer-readable medium having stored therein instructions that are executable to cause the defibrillator to perform a set of acts comprising:
receiving data indicative of a previous shock delivered to a patient by another defibrillator, wherein the data indicative of the previous shock comprises a timestamp associated with the previous shock,
determining that that the timestamp corresponds to a time that is within a threshold time of a current time,
setting an energy level for a subsequent shock based on (i) the data indicative of the previous shock, and (ii) determining that the timestamp corresponds to the time that is within the threshold time of the current time, and
delivering the subsequent shock to the patient at the energy level for the subsequent shock.

16. The defibrillator of claim 15, wherein receiving the data indicative of the previous shock comprises wirelessly receiving the data indicative of the previous shock from a server.

17. The defibrillator of claim 15, wherein receiving the data indicative of the previous shock comprises wirelessly receiving the data indicative of the previous shock from the other defibrillator.

18. The defibrillator of claim 15, wherein the data indicative of the previous shock comprises an energy level of the previous shock, and wherein setting the energy level for the subsequent shock comprises setting the energy level for the subsequent shock based on the energy level of the previous shock.

19. The defibrillator of claim 15, wherein the defibrillator is a monitor defibrillator, and wherein the other defibrillator is an automated external defibrillator.

20. The defibrillator of claim 15, wherein the set of acts further comprises obtaining an instruction to use the data indicative of the previous shock to set the energy level of the subsequent shock, wherein the setting of the energy level of the subsequent shock is further based on the obtaining the instruction.

* * * * *